United States Patent [19]

Fauland et al.

[11] 4,224,438
[45] Sep. 23, 1980

[54] ADENOSINE-5'-CARBOXYLIC ACID AMIDES

[75] Inventors: Erich Fauland, Mannheim-Waldhof; Wolfgang Kampe, Heddesheim; Max Thiel, Mannheim; Karl Dietmann, Mannheim-Vogelstang; Wolfgang Juhran, Mannheim, all of Fed. Rep. of Germany

[73] Assignee: Boehringer Mannheim GmbH, Mannheim, Fed. Rep. of Germany

[21] Appl. No.: 161,338

[22] Filed: Jul. 9, 1971

[30] Foreign Application Priority Data

Jul. 14, 1970 [DE] Fed. Rep. of Germany ....... 2034784
Jul. 14, 1970 [DE] Fed. Rep. of Germany ....... 2034785

[51] Int. Cl.$^2$ ..................... A61K 31/70; C07H 19/18
[52] U.S. Cl. ..................................... 536/26; 424/180; 536/24
[58] Field of Search ................... 260/211.5 R; 536/24, 536/26

[56] References Cited

U.S. PATENT DOCUMENTS

| | | | |
|---|---|---|---|
| 2,831,854 | 4/1958 | Tucker et al. | 260/234 |
| 3,023,183 | 2/1962 | Nelson | 260/234 |
| 3,412,082 | 11/1968 | Thiel et al. | 260/211.5 R |
| 3,575,959 | 4/1971 | Shen et al. | 260/211.5 R |
| 3,697,504 | 10/1972 | Schmidt | 260/211.5 R |

OTHER PUBLICATIONS

Noller, "Chemistry of Organic Compounds," 3rd Ed., W. B. Saunders Co., Phila., Pa., pp. 192-196.

*Primary Examiner*—Johnnie R. Brown
*Attorney, Agent, or Firm*—Sprung, Felfe, Horn, Lynch & Kramer

[57] ABSTRACT

Adenosine-5'-carboxylic acid derivatives of the general formula:

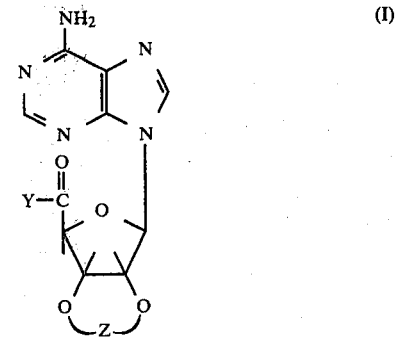

wherein
Z is two hydrogen atoms or a divalent lower alkylidene radical,

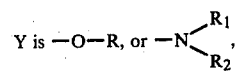

R is an aliphatic or arylaliphatic radical, and
$R_1$ and $R_2$ are independently a hydrogen, hydroxyl, amino, lower alkyl, lower alkenyl, optionally N-alkylated lower aminoalkyl, cycloalkyl, hydroxyalkyl or piperidinyl radical, or
$R_1$ and $R_2$ taken together are a divalent ethylene radical containing 4-7 carbon atoms optionally interrupted by an oxygen or sulfur atom or by an imino, alkylimino or arylimino radical or a pharmacologically compatible salt thereof.

The esters surprisingly can be prepared by esterifying the acid in the presence of sulfuric acid without hydrolyzing the sugar group. While the esters have some activity, they can be used to make the amides which are characterized by marked coronary activity.

13 Claims, No Drawings

ADENOSINE-5'-CARBOXYLIC ACID AMIDES

The present invention is concerned with new esters and amides of adenosine-5'-carboxylic acid and with the preparation thereof and is also concerned with pharmaceutical compositions containing the new adenosine-5'-carboxylic acid derivatives.

The new adenosine-5'-carboxylic acid derivatives according to the present invention are compounds of the general formula:

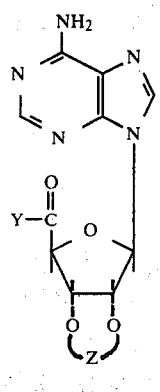

(I)

wherein

Z is two hydrogen atoms or a divalent lower alkylidene radical,

Y is —O—R, or

R is an aliphatic or arylaliphatic radical, and $R_1$ and $R_2$ are independently a hydrogen, hydroxyl, amino, lower alkyl, lower alkenyl, optionally N-alkylated lower aminoalkyl, cycloalkyl, hydroxyalkyl or piperidyl radical, or $R_1$ and $R_2$ taken together are a divalent alkylene radical containing 4-7 carbon atoms optionally interrupted by an oxygen or sulfur atom or by an imino, alkylimino or arylimino radical or a pharmacologically compatible salt thereof.

We have found that the new compounds (I) according to the present invention exhibit circulatory action and the esters, i.e. where Y is —OR, can be converted to the amides whose circulatory activity is markedly great.

The new compounds according to the present invention can be prepared, for example, by the reaction of adenosine-5'-carboxylic acids of the general formula:

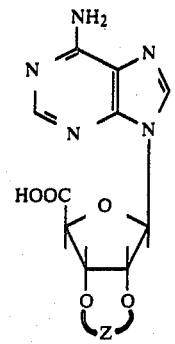

(II)

wherein Z has the same meaning as above, or a reactive derivative thereof, with compounds of the general formula:

R—OH (III), wherein R has the same meaning as above, in the presence of strong mineral acids, whereafter, if desired, the compound (I) thus obtained can be transesterified as with a lower alkanol or converted to an amide by reaction with an amine of the general formula:

$R_1$—NH—$R_2$ (IV), wherein $R_1$ and $R_2$ have the same meaning as above, whereafter, if desired, the product obtained is converted into a pharmacologically compatible salt.

The amides can also be prepared by reacting an amine of formula IV with a reactive derivative of (II) such as the acid halide, anhydride or imidazolide.

It is extremely surprising that, in this particular case, it is possible to carry out the conventional method of esterification of (II) by means of strong mineral acids, especially concentrated sulfuric acid, since it is known than the glycosidic bond in adenosine is extremely easily attacked. In particular, it was not to have been foreseen that the reaction would proceed almost quantitatively or with excellent yields.

For the further working up of the esters of general formula (I), it has proved to be especially favorable to use those compounds of general formula (III) in which R is a lower alkyl radical or an araliphatic radical containing a lower alkylene group.

The esterification of adenosine-5'-carboxylic acid is best carried out at comparatively low temperatures in a large excess of the alcohol component of general formula (III) in the presence of a catalytic amount of a mineral acid. This also applies to the case in which an ester of general formula (I) is to be transesterified.

The adenosine-5'-carboxylic acid used as starting material has already been described (see J.C.S., 1963, p. 1152 and Berichte, 101, 590/1968).

The synthesis of amides by reaction with the amines of formula (IV) takes place in conventional manner in an inert solvent, preferably in methanol, at ambient temperature or with slight warming. However, the solvent can also be omitted and the two reaction components reacted together directly, in which case it is expedient to use the amine in comparatively large excess.

The pharmacologically compatible salts can be obtained in the usual manner, for example, by neutralization with non-toxic inorganic or organic acids, for example, with hydrochloric acid, sulfuric acid, phosphoric acid, hydrobromic acid, acetic acid, lactic acid, citric acid, malic acid, salicyclic acid, malonic acid, maleic acid, succinic acid, and the like.

The new compounds (I) according to the present invention can be administered enterally or parenterally in admixture with solid or liquid pharmaceutical diluents or carriers. As injection medium, it is preferred to use water, which contains conventional additives for injection solutions, such as stabilization agents, solubilizing agents and/or buffers. Additives of this type include for example, tartrate and citrate buffers, ethanol, complex-forming agents (such as ethylene-diamine-tetraacetic acid and the non-toxic salts thereof) and high molecular weight polymers (such as liquid polyethyleneoxide) for the regulation of viscosity. Solid carrier materials include, for example, starch, lactose, mannitol, methyl-cellulose, talc, highly-dispersed silicic acid, high molecular weight fatty acids (such as stearic acid), gelatine, agar-agar, calcium phosphate, magnesium stearate, animal and vegetable fats and solid high molecular weight polymers (such as polyethylene glycols); compositions suitable for oral administration can, if desired, also contain flavoring and/or sweetening agents.

The following Examples are given for the purpose of illustrating the present invention:

EXAMPLE 1

Adenosine-5'-carboxylic acid methyl ester (a) 46 g of adenosine-5'-carboxylic acid are introduced into a mixture of 1.4 liters of anhydrous methanol and 15 ml of concentrated sulfuric acid and the mixture boiled for 45 minutes. The slightly cloudy solution obtained is filtered and mixed with a solution of 27 g of sodium bicarbonate in 1 liter of water. A further 500 ml of water are added to the neutralized reaction mixture which is then left to stand overnight in a refrigerator to crystallize. The crystalline material obtained is filtered off with suction and dried in a vacuum drying cabinet. There are thus obtained 47 g (92% of theory) of adenosine-5'-carboxylic acid methyl ester, which has a melting point of 215°-217° C.

(b) In an analogous manner, by the reaction of free adenosine-5'-carboxylic acid with ethanol, there is obtained adenosine-5'-carboxylic acid ethyl ester in a yield of 78% of theory (m.p. 204°-205° C.) and by the reaction of free adenosine-5'-carboxylic acid with n-butanol, there is obtained adenosine-5'-carboxylic acid n-butyl ester in a yield of 54% of theory (m.p. 167° C.).

EXAMPLE 2

2',3'-O-Isopropylidene-adenosine-5'-carboxylic acid methyl ester 10 g of 2',3'-O-isopropylidene-adenosine-5'-carboxylic acid are dissolved in 400 ml of methanol and mixed with 6 ml of concentrated sulfuric acid. The reaction mixture is left to stand for 4 hours at ambient temperature and then neutralized with 17 g of sodium bicarbonate in 200 ml of water. The product which precipitates out is filtered off with suction and successively washed with 5% aqueous sodium bicarbonate solution, water and a little methanol and then dried. There are obtained 10.4 g of 2',3'-O-isopropylidene-adenosine-5'-carboxylic acid methyl ester, which has a melting point of 239°-240° C. The yield is 74% of theory.

EXAMPLE 3

Adenosine-5'-carboxylic acid n-butyl ester 5 g of adenosine-5'-carboxylic acid methyl ester are dissolved in 200 ml of n-butanol and, together with 3 g of D-benzedrine, boiled under reflux for 3 hours. The reaction mixture is filtered and the filtrate evaporated in a vacuum. The evaporation residue is triturated with ether, filtered off with suction, again washed with ether and dried. There are thus obtained 5.6 g of adenosine-5'-carboxylic acid n-butyl ester, which has a melting point of 166°-167° C. The yield is 87% of theory. The crude product obtained can be recrystallized from water.

EXAMPLE 4

Adenosine-5'-carboxylic acid-n-hexyl ester 5 g of adenosine-5'-carboxylic acid are dissolved in 200 ml of n-hexanol and 2 ml of concentrated sulfuric acid and heated to 100° C. for 3 hours. After cooling, the reaction mixture is neutralized with triethylamine and left to stand overnight, the desired n-hexyl ester and triethylamine sulfate thereby crystallizing out. After filtering off with suction, the triethylamine sulfate is washed out with water and the remaining ester is recrystallized from methanol. There are obtained 3.1 g (48% of theory) of adenosine-5'-carboxylic acid n-hexyl ester, which has a melting point of 145°-147° C.

EXAMPLE 5

Adenosine-5'-carboxylic acid benzyl ester 5 g of adenosine-5'-carboxylic acid methyl ester are suspended in 200 ml of benzyl alcohol, with the addition of 7 g of triethylamine, and the reaction mixture heated to 100° C. for 5 hours, the methyl ester thereby going into solution. After termination of the reaction, the base and excess alcohol are stripped off in a vacuum, the residue is triturated with ether for the removal of traces of amine and solvent and, after filtering off with suction, the product is recrystallized from water. There are thus obtained 3.3 g (53% of theory) of adenosine-5'-carboxylic acid benzyl ester, which has a melting point of 144°-145° C.

EXAMPLE 6

Adenosine-5'-carboxamide 5 g of adenosine-5'-carboxylic acid methyl ester as produced in Example 1a are mixed with 100 ml of 25% methanolic ammonia solution. A clear solution is obtained from which, after standing for some time, crystals separate out. There are thus obtained 4.1 g of adenosine-5'-carboxamide, which has a melting point of 244°-245° C. After recrystallization from water, this compound has a melting point of 249°-250° C. The yield is 91% of theory.

EXAMPLE 7

2',3'-O-Isopropylidene-adenosine-5'-carboxamide (a) Variant A:

10 g of 2',3'-O-isopropylidene-adenosine-5'-carboxylic acid are allowed to react for 4 hours at ambient temperature with 0.4 liters of anhydrous methanol and 6 ml of concentrated sulfuric acid, whereafter the reaction mixture is neutralized with sodium bicarbonate and then worked up in the manner described in Example 2. The 2',3'-O-isopropylidene-adenosine-5'-carboxylic acid methyl ester thus obtained has a melting point of 239°–240° C.

2.5 g of 2′,3′-O-isopropylidene-adenosine-5′-carboxylic acid methyl ester are suspended in 250 ml of 25% methanolic ammonia and the reaction mixture stirred for 4 days at ambient temperature in a glass autoclave. The substance which separates is filtered off with suction and recrystallized from water. There is obtained 1.7 g (60% of theory) of 2′,3′-O-isopropylidene-adenosine-5′-carboxamide, which melts, with decomposition, at 214°–216° C.

(b) Variant B:

2′,3′-O-isopropylidene-adenosine-5′-carboxylic acid is heated with thionyl chloride/dimethyl formamide. Upon cooling, the acid chloride separates out from the reaction mixture in crystalline form and, after filtering off with suction and washing with anhydrous chloroform and ether, is further reacted as follows:

5.5 g of 2′,3′-O-isopropylidene-adenosine-5′-carboxylic acid chloride are dissolved in 50 ml of 25% methanolic ammonia and left to stand overnight at ambient temperature. The solvent is then distilled off in a vacuum and the residue recrystallized from water. There are obtained 2.4 g (46% of theory) of 2′,3′-O-isopropylidene-adenosine-5′-carboxamide, which has a melting point of 216° C.

EXAMPLE 8

Adenosine-5′-carboxylic acid N-allylamide (a) 5 g of adenosine-5′-carboxylic acid methyl ester are suspended in 150 ml of methanol, mixed with 15 g of allylamine and stirred, while warming, for 1 hour. The resultant clear solution is left to stand for 2 days at ambient temperature and the crystalline precipitate thereafter filtered off with suction and the mother liquor concentrated. The crude product thus obtained is recrystallized from methanol. There are thus obtained 2.8 g (54% of theory) of adenosine-5′-carboxylic acid N-allylamide, which has a melting point of 189°–190° C.

In an analogous manner, there are obtained, by the reaction of adenosine-5′-carboxylic acid methyl ester:

(b) with methylamine: adenosine-5′-carboxylic acid N-methylamide; m.p. 237°–238° C.; yield 45% of theory;

(c) with ethylamine: adenosine-5′-carboxylic acid N-ethylamide; m.p. 220°–222° C.; yield 67% of theory;

(d) with hydroxyethylamine: adenosine-5′-carboxylic acid N-(β-hydroxyethyl)-amide; m.p. 198°–199° C.; yield 58% of theory;

(e) with isopropylamine: adenosine-5′-carboxylic acid N-isopropylamide; m.p. 145°–147° C.; yield 53% of theory;

(f) with butylamine: adenosine-5′-carboxylic acid N-n-butylamide; m.p. 109°–111° C.; yield 88% of theory;

(g) with isobutylamine: adenosine-5′-carboxylic acid N-isobutylamide; m.p. 194°–196° C.; yield 85% of theory; and (h) with dimethylaminoethylamine: adenosine-5′-carboxylic acid N-(2-dimethylaminoethyl)-amide; m.p. 136°–138° C.; yield 84% of theory.

EXAMPLE 9

Adenosine-5′-carboxylic acid N-cyclopentylamide (a) 5 g of adenosine-5′-carboxylic acid methyl ester are heated for 30 minutes on a steambath, together with 20 ml of cyclopentylamine, a clear solution being obtained. Thereafter, excess amine is distilled off and the residue is washed with ether and subsequently recrystallized from methanol and isopropanol. There are thus obtained 2.4 g (43% of theory) of adenosine-5′-carboxylic acid N-cyclopentylamide, which has a melting point of 201°–202° C.

In an analogous manner, there are obtained, by the reaction of adenosine-5′-carboxylic acid methyl ester:

(b) with cyclohexylamine: adenosine-5′-carboxylic acid N-cyclohexylamide; m.p. 134°–136° C.; yield 50% of theory;

(c) with morpholine: adenosine-5′-carboxylic acid morpholide; m.p. 248°–249° C.; yield 37% of theory;

(d) with piperidine: adenosine-5′-carboxylic acid N,N-pentamethylene-amide; m.p. 225°–226° C.; yield 44% of theory; and (e) with N-methyl-piperazine: adenosine-5′-carboxylic acid N,N-(3-methyl-3-azapentamethylene)-amide; m.p. 155°–157° C.; yield 48% of theory.

EXAMPLE 10

Adenosine-5′-hydroxamic acid 5 g of adenosine-5′-carboxylic acid methyl ester in alcoholic solution are mixed with an excess of hydroxylamine, briefly heated to 60° C. until a clear solution is obtained and then, without additional heating, stirred for a further 2 hours. The crystalline precipitate obtained is filtered off with suction and recrystallized from water. There are thus obtained 4.0 g of adenosine-5′-hydroxamic acid, which melts, with decomposition, at 224°–225° C. The yield is 83% of theory.

EXAMPLE 11

Adenosine-5′-carboxylic acid hydrazide 5 g of adenosine-5′-carboxylic acid methyl ester are suspended in 150 ml of methanol mixed with 20 ml of hydrazine hydrate and heated to the boil. The ester thereby goes into solution, while, almost simultaneously, the hydrazide precipitates out in the form of a fine crystalline material. After standing overnight, it is filtered off with suction, washed with methanol and dried. There are obtained 4.4 g of adenosine-5′-carboxylic acid hydrazide, which melts, with decomposition, at 270°–272° C. The yield is 93% of theory. The compound can be readily recrystallized from hot water.

EXAMPLE 12

2′,3′-O-Isopropylidene-adenosine-5′-carboxylic acid N,N-dimethylamide 5 g of 2′,3′-O-isopropylidene-adenosine-5′-carboxylic acid chloride are dissolved in 50 ml of a 25% solution of dimethylamine in methanol and left to stand for 1 day at ambient temperature. Excess amine and methanol are then stripped off in a vacuum and the residue is dissolved in chloroform and this solution washed twice with water. The chloroform solution is dried over anhydrous calcium chloride, the chloroform is distilled off and the residue is dried in a vacuum. There are thus obtained 2.3 g (44% of theory) of 2′,3′-O-isopropylidene-adenosine-5′-carboxylic acid N,N-dimethylamide in the form of amorphous, very glossy flakes. The structure of the product was confirmed by the mass spectrum.

against the initial value. High figures therefore mean a strong circulatory action.

TABLE

| Example | Amides corresponding to the amines listed below | Dosage mg/kg i.v. | Reduction of Arterio-Sinuous $O_2$-difference $(AV_cDO_2)$ in % by Volume Compared to Initial Value |
|---|---|---|---|
| Control-Adenosine-5'-carboxylic acid | — | 0.2 | 0.3 |
|  |  | 0.4 | 1.0 |
| 6 | Ammonia | 0.2 | 9.6 |
| 7 (isopropylidene) | Ammonia | 0.4 | 1.9 |
| 8a | Allylamine | 0.2 | 6.8 |
| 8b | Methylamine | 0.2 | 12.1 |
| 8c | Ethylamine | 0.2 | 9.2 |
| 8d | Hydroxyethylamine | 0.1 | 8.9 |
| 8e | Isopropylamine | 0.2 | 9.1 |
| 8f | Butylamine | 0.4 | 7.5 |
| 8g | Isobutylamine | 0.2 | 8.3 |
| 8h | Dimethylaminoethylamine | 0.2 | 8.8 |
| 9a | Cyclopentylamine | 0.2 | 12.9 |
| 9b | Cyclohexylamine | 0.4 | 1.4 |
| 9c | Morpholine | 0.4 | 1.3 |
| 10 | Hydroxylamine | 0.4 | 10.3 |
| 11 | Hydrazine | 0.2 | 7.4 |
| 14 | N-aminopiperidine | 0.4 | 2.6 |

EXAMPLE 13

Adenosine-5'-carboxylic acid N-tert.-butylamide 5 g of adenosine-5'-carboxylic acid methyl ester are heated together with 100 ml of tert.-butylamine on a streambath until a clear solution is obtained and thereafter the reaction mixture is left to stand for 16 hours at ambient temperature. Excess tert.-butylamine is then distilled off and the residue is mixed with methanol, again evaporated to dryness and the solid residue, after slurrying in cold methanol is filtered off with suction. After recrystallizing twice from a little methanol, there are obtained 2.15 g (38% of theory) of adenosine-5'-carboxylic acid N-tert.-butylamide, which melts, with decomposition, at 279°–280° C.

EXAMPLE 14

Adenosine-5'-carboxylic acid N-piperidinoamide 5 g of adenosine-5'-carboxylic acid methyl ester and 25 g of N-aminopiperidine are heated on a steambath for 2 hours. The reaction mixture is thereafter cooled and the product precipitated out by the addition of 350 ml of ether. The solid precipitate is filtered off with suction and recrystallized from methanol. There are thus obtained 2.6 g (42% of theory) of adenosine-5'-carboxylic acid N-piperidinoamide, which has a melting point of 189°–191° C.

The novel compounds were tested as follows: Catheters were implanted operatively in the sinus coronarious, aorta and the vena cava of dogs. Thus, it was possible to determine photometrically the coronary-sinuous oxygen saturation by withdrawing a blood sample and, by taking into account the actual hemoglobin values, to obtain a value for % by volume. A reduction of the oxygen extraction due to the effect of the test substances evidences an improvement of the oxygen supply to the heart which is the therapeutic aim of all coronary dilators (unless major changes of the myocardiac oxygen consumption occur).

The following test results set forth in % by volume the reduction of the coronary-sinuous oxygen difference measured at the moment of maximum effect as Adenosine-5'-carboxylic acid was selected as reference compound. On intravenous administration, this compound dilates the vessels. Especially in the coronary system this vasodilation results in a circulation increase. When comparing the effectiveness of the products according to the invention it can be seen that all the amides are superior to adenosine-5'-carboxylic acid. The amides corresponding to ammonia, hydroxylamine, isobutylamine, dimethylamino-ethylamine, methylamine, ethylamine, isopropylamine, cyclopentylamine and hydroxyethylamine are especially active. Though not included in the table, the adenosine-5'-carboxylic acid esters also are active, though not to the same extent as the amides.

It will be appreciated that the instant specification and examples are set forth by way of illustration and not limitation, and that various modifications and changes may be made without departing from the spirit and scope of the present invention.

What is claimed is:

1. Adenosine-5'-carboxylic acid derivatives of the general formula:

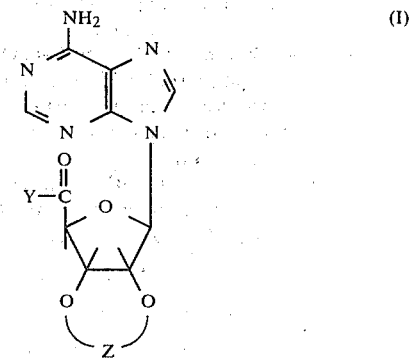

wherein

Z is two hydrogen atoms or a divalent lower alkylidene radical,

Y is —O—R, or

R is a phenyl lower alkyl radical, and

R₁ and R₂ are independently a hydrogen, hydroxyl, amino, lower alkyl, lower alkenyl, optionally N-alkylated lower aminoalkyl, cycloalkyl, hydroxyalkyl or a piperidyl radical, or R₁ and R₂ taken together are a divalent alkylene radical containing 4—7 carbon atoms, or R₁ and R₂ taken together with the nitrogen atom are a piperidyl, morpholinyl, piperazinyl or methylpiperazinyl radical, or a pharmacologically compatible salt thereof.

2. Compound according to claim 1 wherein Y is

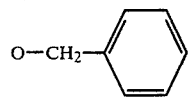

3. Compound according to claim 1 wherein

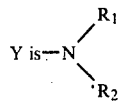

and R₁ and R₂ are as defined in claim 1, or a pharmacologically compatible salt thereof.

4. Compound according to claim 1 wherein R₁ is hydrogen, R₂ is hydrogen, hydroxyl, isobutyl, dimethylaminoethyl, methyl, ethyl, isopropyl, cyclopentyl or hydroxyethyl, and Z is two hydrogen atoms.

5. Compound according to claim 1 wherein such compound is adenosine-5'-carboxylic acid amide.

6. Compound according to claim 1 wherein such compound is adenosine-5'-carboxylic acid N-ethylamide.

7. Compound according to claim 1 wherein such compound is adenosine-5'-carboxylic acid N-isopropylamide.

8. Compound according to claim 1 wherein such compound is adenosine-5'-carboxylic acid N-hydroxyethylamide.

9. Compound according to claim 1 wherein such compound is adenosine-5'-carboxylic acid N-methylamide.

10. Compound according to claim 1 wherein such compound is adenosine-5'-carboxylic acid N-cyclopentylamide.

11. Compound according to claim 1, wherein R₁ is hydrogen, R₂ is hydrogen, hydroxyl, amino, allyl, methyl, ethyl, hydroxyethyl, isopropyl, butyl, isobutyl, dimethylaminoethyl or cyclopentyl, and Z is two hydrogen atoms.

12. Adenosine-5'-carboxyamide of the formula

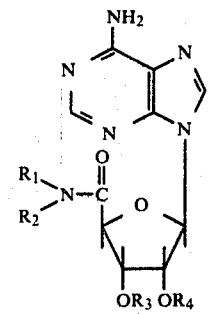

wherein R₁ and R₂ are each selected from the group consisting of hydrogen, lower alkyl, hydroxy lower alkyl, lower cycloalkyl, lower alkenyl, lower alkyl amino lower alkyl or R₁ and R₂ when taken together with the nitrogen atom form a 5 or 6 membered hetero cyclic moiety; R₃ and R₄ are hydrogen or when taken together form an isopropylidene moiety; and the pharmaceutically acceptable acid addition salts thereof.

13. Adenosine-5'-carboxyamide of the formula

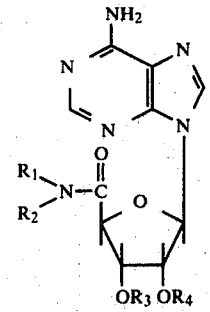

wherein R₁ and R₂ are each selected from the group consisting of hydrogen, lower alkyl, hydroxy lower alkyl, lower cycloalkyl, lower alkenyl, lower alkyl amino lower alkyl; R₃ and R₄ are hydrogen or when taken together form an isopropylidene moiety; and the pharmaceutically acceptable acid addition salts thereof.

* * * * *